United States Patent [19]
Kira

[11] Patent Number: 5,864,070
[45] Date of Patent: Jan. 26, 1999

[54] APPARATUS AND METHOD FOR DETECTING SIZING OR MARGINAL GRADATION CHANGES OF A CONTROLLED OR RANDOM SIZED PRODUCT ON A CONVEYING MEDIUM

[76] Inventor: Alan K. Kira, 1327 Kamehamha IV Rd., Honolulu, Hi. 96819

[21] Appl. No.: 818,566

[22] Filed: Mar. 12, 1997

[51] Int. Cl.[6] .................................................. G01M 19/00
[52] U.S. Cl. ...................................... 73/865.8; 235/98 B
[58] Field of Search .......................... 73/865.8; 340/673, 340/674, 675; 235/98 B, 132 E; 377/8, 19

[56] References Cited

U.S. PATENT DOCUMENTS

| | | | |
|---|---|---|---|
| 853,971 | 5/1907 | Greene | 377/8 |
| 3,577,955 | 5/1971 | Palmer | 235/98 B |
| 3,702,925 | 11/1972 | Anderson et al. | 325/98 B |
| 4,539,470 | 9/1985 | Honegger et al. | 235/98 B |
| 4,665,392 | 5/1987 | Koontz . | |
| 4,713,831 | 12/1987 | Morisod . | |

*Primary Examiner*—Elizabeth L. Dougherty
*Assistant Examiner*—Paul D. Amrozowicz
*Attorney, Agent, or Firm*—Shlesinger, Arkwright & Garvey LLP

[57] ABSTRACT

Apparatus and method apparatus for detecting marginal gradation changes of a controlled product on a conveyor. The apparatus comprises a transducer (4) for converting swinging motion to a number of pulses; a member (24) operably secured to the transducer, the member for being in contact with the controlled product to cause the member to swing back and forth, thereby causing the transducer to generate the number of pulses; and a programmable device (28) operably connected to the transducer, the device being adapted to count the number of pulses generated by the transducer over several blocks of time periods, compare the number in each block of time to a group of reference numbers for the product, sum the number of occurrences that the number is above or below the group of reference numbers and provide an indication when the sum exceeds a target value.

22 Claims, 7 Drawing Sheets

APPARATUS AND METHOD FOR DETECTING SIZING OR MARGINAL GRADATION CHANGES OF A CONTROLLED OR RANDOM SIZED PRODUCT ON A CONVEYING MEDIUM

RELATED APPLICATIONS

This is a non-provisional continuation-in-part application based on a provisional application Ser. No. 60/013,283 filed on Mar. 12, 1996.

FIELD OF THE INVENTION

The present invention pertains to apparatus and method for detecting marginal gradation changes of a controlled product, such as processed rock from a mine and quarry operation, grain from feed mills, coal, and other processible solid materials, nuts and bolts, screws, etc. and monitoring relative size changes of the controlled product while being transported by a conveying media, such as conveyor belts.

BACKGROUND OF THE INVENTION

There are thousands of processes involving the use of conveyors throughout the world. Associated with the use of conveying systems is the need for a simple, easily maintainable, highly reliable, intelligent system, that will, within reasonable limits, monitor gradation variations of a material or product after it has gone through a process, such as rock crushing.

Designing a system to monitor and generate the entire gradation spectrum of a controlled product "on-the-fly" would be extremely involved and complex, maintenance intensive and very costly. Most processing facilities maintain quality control technicians who periodically sample the material to verify output product against a known standard. However, there is a need for an apparatus that will monitor the product between scheduled sample periods. It is, therefore, an extremely useful complement to the existing quality control scheme in the monitoring of conveyed products, enabling the user to view and identify reasonable variations in the gradation of the controlled products when compared to a reference sample and assist in the identification of the materials or products.

OBJECTS AND SUMMARY OF THE INVENTION

It is an object of the present invention to provide apparatus and method for detecting and recording increasing gradation changes on a processed product on a conveyor, such as crushable rock products. The gradation changes can be used, as in a rock crushing operation, to warn of crusher close side setting openings or for automatically adjusting crusher openings.

It is another object of the present invention to provide apparatus and method for detecting material contamination on a product being conveyed, such as in a quarry operation, feed mill, or processing plant having different feed products on a feed mill operation (sugar and flour, etc.).

It is yet another object of the present invention to provide apparatus and method for indicating the presence of a product on a conveyor and its identification where the conveying system is hidden from view or closed off to human access for environmental or safety purposes.

It is still an object of the present invention to provide apparatus and method that monitor the product in the conveyor and provide information to alert quality control technicians of potential problems at in-between scheduled sample times.

It is an object of the present invention to provide apparatus and method for determining whether the controlled product is drifting outside design margins, or is being altered by contamination of a foreign material.

In summary, the present invention provides apparatus and method for detecting marginal gradation changes of a controlled product on a conveyor.

The apparatus comprises a rotatable shaft; a rotary encoder sensor operably connected to the shaft, such that rotational motion of the shaft is converted to a number of pulses by the rotary encoder sensor; a member operably secured to the shaft, the member for being in contact with the controlled product to cause the member to swing back and forth and impart rotary motion to the shaft; and a programmable device operably connected to the rotary encoder sensor adapted to count the number of pulses generated by the rotary encoder sensor over several blocks of time periods, compare the number in each block of time to a group of reference numbers for the product, sum the number of occurrences that the number is above or below the group of reference numbers and initiate an external device, such as an alarm, when the sum exceeds a target value.

The method includes the steps of contacting the moving product with a member so that the member swings back and forth, converting the swinging motion to a number, counting the number over several blocks of time periods, comparing number in each block of time to a group of reference numbers for the product, summing the number of occurrences that the number is above or below the group of reference numbers and initiating output signal, such as an alarm, when the sum exceeds a target value.

The apparatus and method can also be used to detect the presence and identity of the product on the conveyor.

These and other objects of the present invention will become apparent from the following detailed description.

BRIEF DESCRIPTIONS OF THE DRAWINGS

FIGS. 4A, 4B, 4C and 4D together comprises a flow chart of a program used in the present invention.

DETAILED DESCRIPTION OF THE INVENTION

Figure 1:
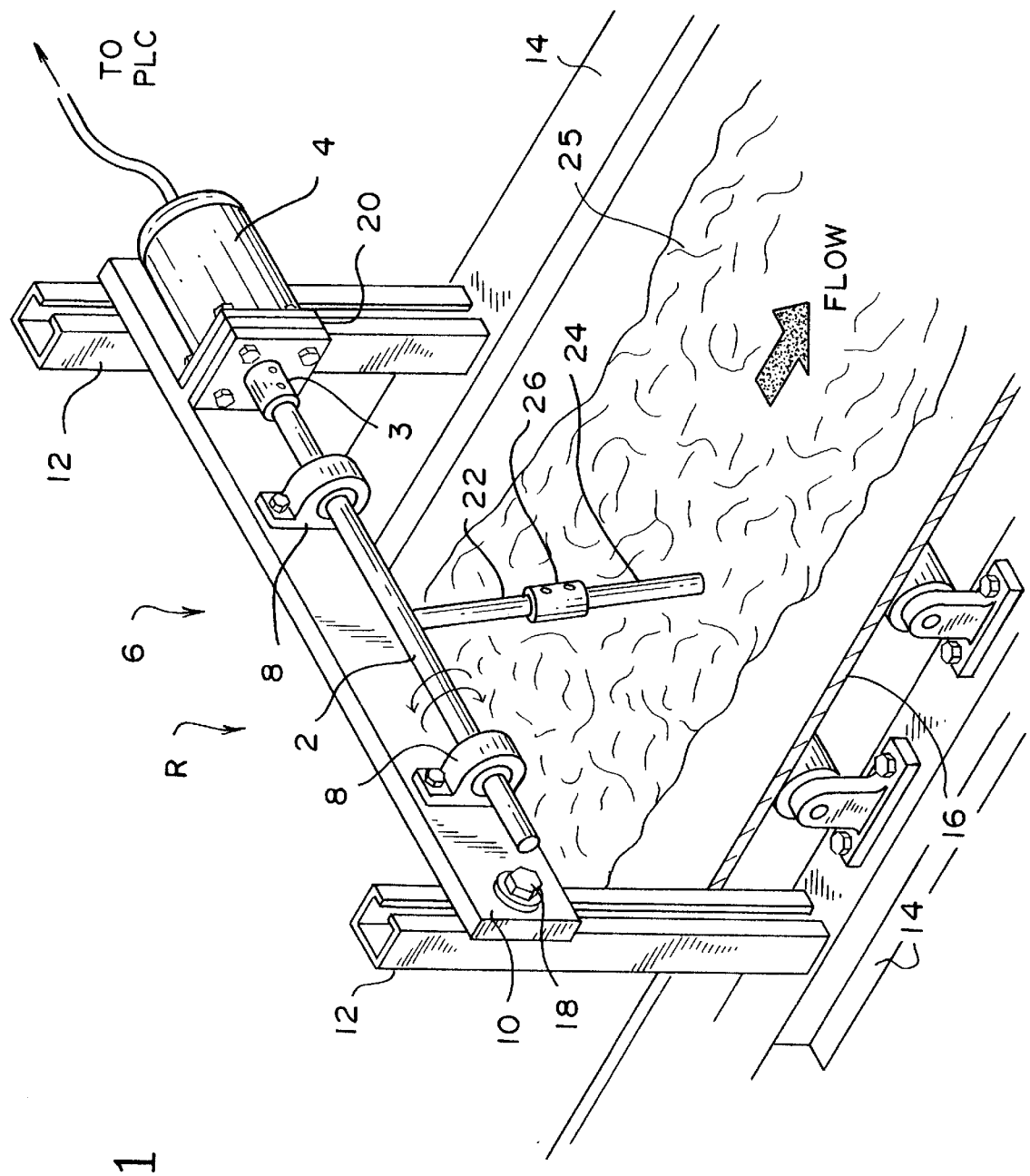
FIG. 1 is a perspective view of a rotary sensor assembly made in accordance with the present invention.
Figure 2:
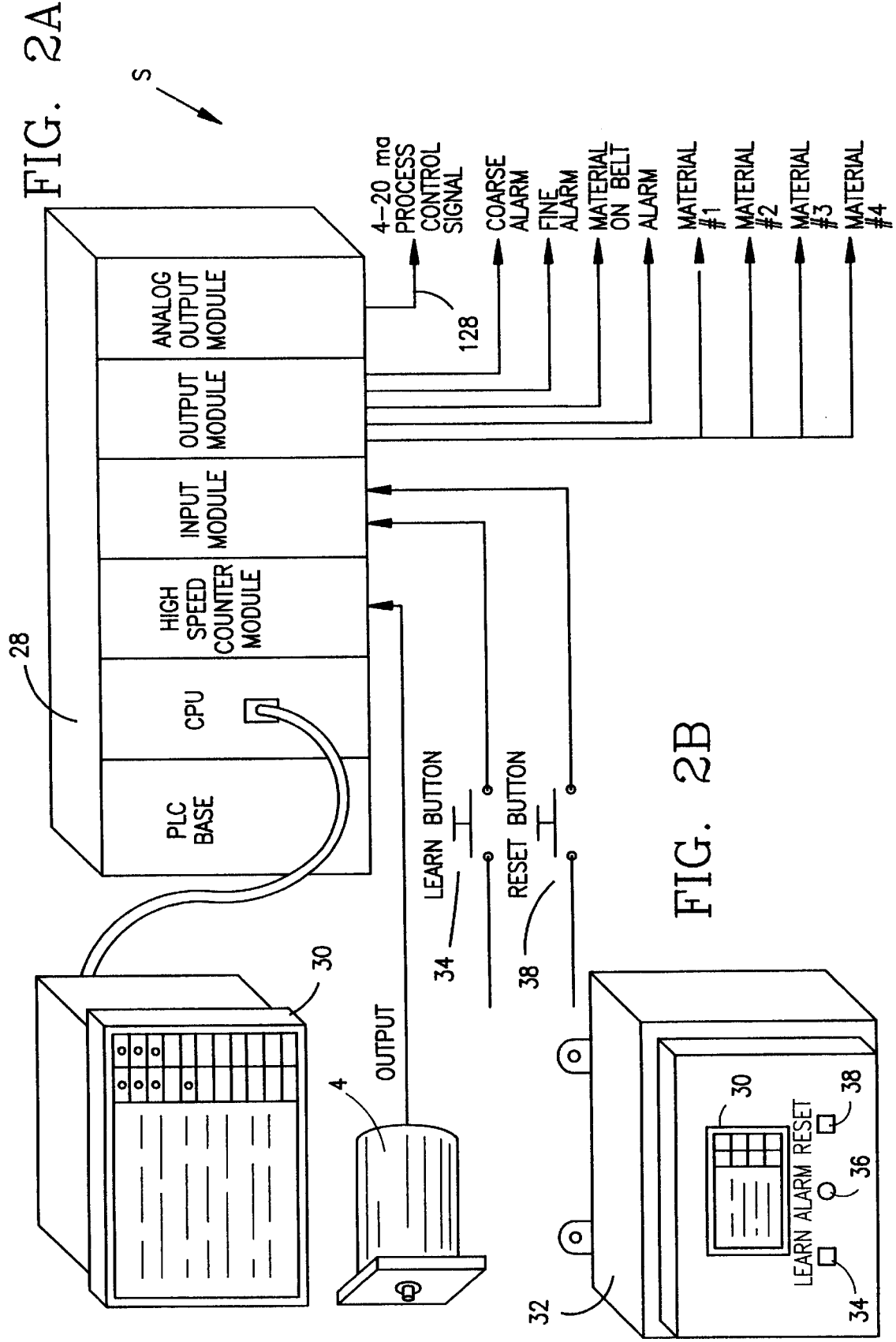
FIG. 2A is a schematic diagram of an electronic system used to process the information from the rotary sensor assembly of FIG. 1 in accordance with the presence invention.
FIG. 2B is perspective view of a housing for the electronic system of FIG. 2A.

The apparatus made in accordance with the present invention comprises a rotary sensor assembly R and an electronic system S, as best shown in FIGS. 1 and 2A. The sensor R includes a rotary shaft 2 operably coupled via a coupling 3 to a transducer, such as a rotary encoder sensor 4 secured to a frame assembly 6, as best shown in FIG. 1. The rotary encoder sensor 4 converts rotary or swinging motion to an electrical output, such as pulse train. The rotary shaft 2 is held by a pair of shaft bearings 8 secured to a flat mounting plate 10, which is in turn secured to a pair of spaced apart channel members 12, which are secured to the conveyor frame 14. The mounting plate 10 is selectively positionable vertically above the conveyor belt 16 along the lengths of the channel members 12 by means of a pair of bolts 18.

The rotary encoder sensor 4 is secured to a transversely mounted flange 20 as best shown in FIG. 1.

A rod 22 is transversely secured to an intermediate portion of the shaft 2. A sensor member 24 is secured to the free end of the rod 22 by means of a coupler 26. The sensor member 24 is, therefore, advantageously replaceable as the need arises, such as when it breaks down or wears out or provide a different weight to change its dynamical response to the product being monitored. The vertical adjustability of the mounting plate 10 advantageously provides for fine-tuning the position of the sensor member 24 and thereby change its dynamical response to the product 25 being monitored.

The output of the rotary encoder sensor 4 is fed to a programmable device 28, such as a programmable logic controller, as best shown in FIG. 2A.

The programmable device 28 contains the Main System Program (MSP), as will be described below, for translating the pulses generated by the rotary encoder sensor 4 from the swinging motion of the sensor member 24, to produce information for the user in monitoring and recording, and alarming control of external devices. An operator interface terminal (OIT) 30 is used to configure the MSP by entering operational parameters and for displaying status and data fields. The OIT 30 is operably connected to the programmable device 28. A control panel 32 provides a compact housing for the programmable device 28, the operator interface terminal 30, a LEARN pushbutton 34, an alarm indicator light 36 and a reset push button 38, as best shown in FIG. 2B.

Output devices such as relays, indicator lights, alarms, etc., are connected to the output of the programmable device 28. External devices such as controllers, personal computers, etc., may also be connected to the output of the programmable device 28.

The apparatus of the present invention converts the swinging motion of the sensor member 24 as it works off the surface of, and sometimes slightly penetrating into, the material 25 being conveyed below, depending upon the hardness and composition of the material on the conveying means, into a number of pulses by means of the rotary encoder sensor 4. A person of ordinary skill in the art will understand that the number of pulses generated by the rotary encoder sensor 4 is directly proportional to the amplitude or arc of swing of the sensor member. Consequently, as the product gets coarser, the sensor member 24 will bounce more wildly and thus produce greater number of pulses. Conversely, as the product gets finer, the sensor member 24 will bounce less, producing less number of pulses.

The pulses produced are counted and processed by the MSP in the programmable device 28 to provide the user with outputs and information which can be further processed for monitoring, recording, alarm and control of external devices, providing the means to identify the product and alert the user on material variation.

Twelve parameters are entered via the operator interface terminal 30 to configure the MSP operation within a desirable level for a particular application. These parameters are discussed below.

1. Learning Time (and Sample Time): XX.X seconds. This is the time block in which the MSP will scan the material to "LEARN" the characteristics of the flow. This is also the SAMPLE time for the MSP during the MONITORING mode.
2. Group Cycle: XX CYCLES. This is the number of samples that will be viewed together as a GROUP during the MONITORING mode. Each sample is produced by a monitor cycle routine within the MSP.
3. Failure %: XX Percentage. This is the percentage of the maximum allowable difference between the LEARN data or characteristics and the SAMPLE, as will be explained below.
4. LEARN % Tolerance: XX Percentage. This is the percentage of the mean, or average of the LEARN samples, to be used in self-checking each sample during the LEARN mode against excessive variations before acceptance, as will be explained below.
5. Material #1: MAPP#. Entering a material #1 MAPP# will cause the MSP to output a signal from the programmable device 28 each time the conveyed product produces a MAPP# within the tolerance margins or material identification of the monitored product.
6. Material #2: MAPP#. Entering a material #2 MAPP# will cause the MSP to output a signal from the programmable device 28 each time the conveyed product produces a MAPP# within the tolerance margins or material identification of the monitored product.
7. Material #3 MAPP#. Entering material #3 MAPP# will cause the MSP to output a signal from the programmable device 28 each time the conveyed product produces a MAPP# within the tolerance margins, or material identification of the monitored product.
8. Material #4: MAPP#. Entering a material # for MAPP# will cause the MSP to output a signal from the programmable device 28 each time the conveyed product produces a MAPP# within the tolerance margins, or material identification of the monitored product.
9. Material Tolerance: XX Percentage. This is the percentage tolerance margins for materials #1, #2, #3, and #4 setting. For example, Material #1 MAPP#=500, and Tolerance=0.10
MAPP #1 Tolerance=500×0.10=50.
Therefore,
The range for Material #1 MAPP# is,
MAPP #1−Tolerance≦MAPP#≦MAPP #1+Tolerance, or
450≦MAPP#≦550.

10. Mode: 1, 2, 3.

Mode 1: Normal Operation. The MSP will monitor the LEARNED material for VG+ and VG− with "Coarse" and "Fine" alarms.

Mode 2: Multiple Material Identification. No VG+ or VG− and, therefore, no "Coarse" and "Fine" alarms. Mode 2 is used to identify an unknown material on the conveyor belt that has been LEARNED before. It is also used to find the closest match between the present MAPP# and the Material #1, #2, #3 or #4 MAPP#.

Material #1 MAPP# will output a signal each time the MAPP# of the sample falls within the margins determined by the Material Tolerance and will become the MAPP# for the material for identification purposes.

Material #2 MAPP# will output a signal each time the MAPP# of the sample falls within the margins determined by the Material Tolerance and will become the MAPP# for the material for identification purposes.

Material #3 MAPP# will output a signal each time the MAPP# of the sample falls within the margins determined by the Material Tolerance and will become the MAPP# for the material for identification purposes.

Material #4 MAPP# will output a signal each time the MAPP# of the sample falls within the margins determined by the Material Tolerance and will become the MAPP# for the material for identification purposes.

Mode 3: Uses the previous mentioned MAPP#'s for the Materials #1, 2, 3 and 4, for comparative purposes. As in Mode 2, there are no VG+ and VG− and, therefore, no "Coarse" and "Fine" alarms.

Material #1: MAPP#1 with options =, <, and >.
Material #2: MAPP#1 with options =, <, and >.
Material #3: MAPP#1 with options =, <, and >.
Material #4: MAPP#1 with options =, <, and >.

11. # MTL LRN: Selects the number of materials that the MSP will need to LEARN for identification or comparison modes.
12. MA RANGE: Sets the 20 ma point for the 4–20 ma output signal to recorders or process controllers.

Following entry of the twelve parameters as discussed above via the operator interface terminal at 30, the MSP is ready to LEARN the controlled product or material to be monitored.

The LEARN routine produces the reference information that the MSP will use to compare each and every sample that it takes from that point on during the MONITORING mode until another LEARN routine is initiated. The reference data produced from the LEARN routine resides in memory and will continuously be used as the comparison source until another LEARN sequence is initiated. Therefore, it is critical that a good representative sample of the material or product is working the apparatus through the sensor member 24 for the length of the LEARN cycle.

Figure 3:
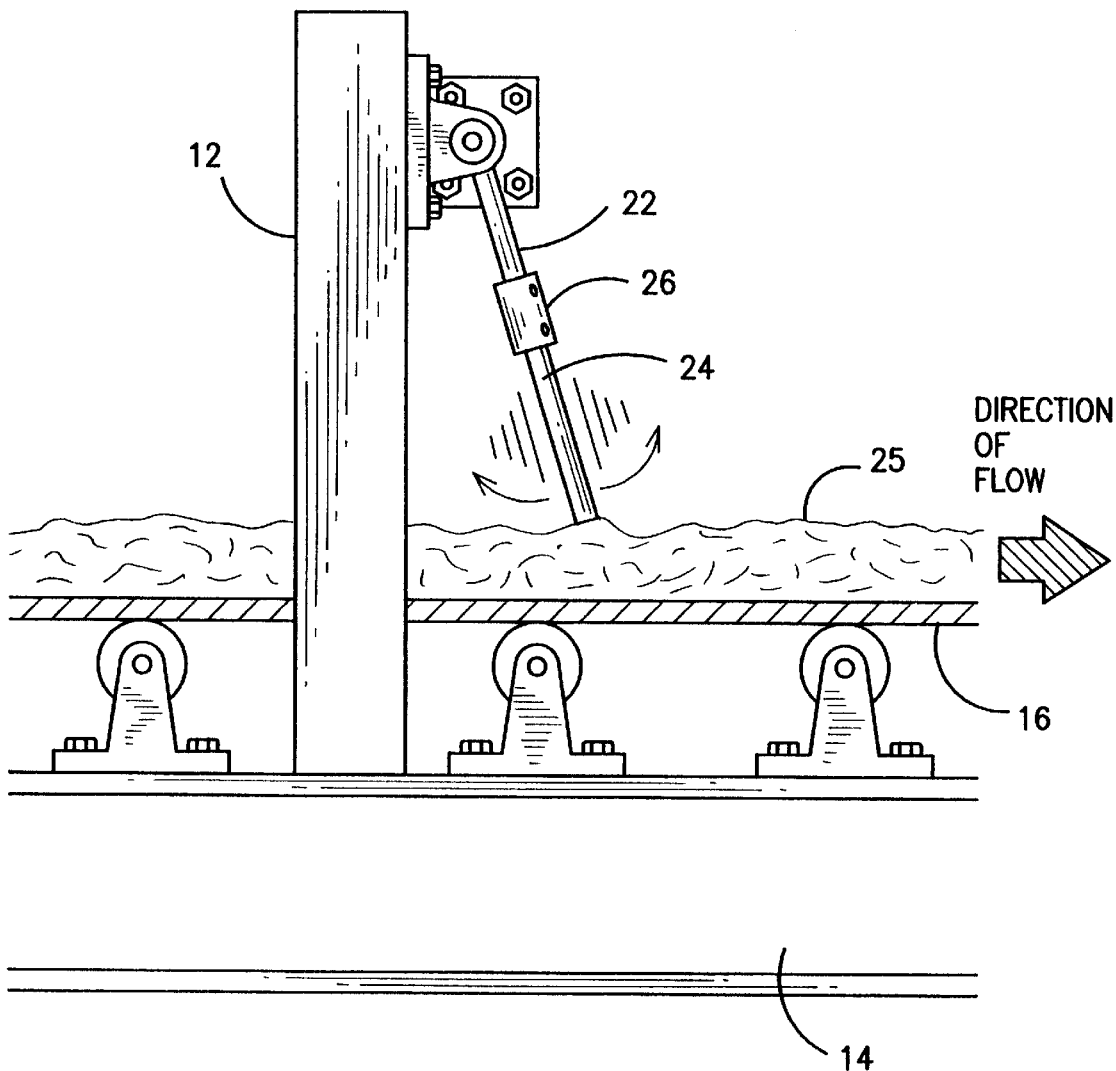
FIG. 3 is a side elevational view of FIG. 1, showing the angular swinging motion of a sensor arm to detect and monitor a product being conveyed by a conveyor.

The MSP constantly samples what is on the conveying means and generates a Material Angular Pitch Pulse No. (MAPP#, pronounced MAPP No.). The MAPP# is the result of the physical dynamics of the sensor member 24 impacting and working off the material 25 on the conveying means, as influenced by the conveying speed of the material, the angle of attack of the material, referred to as pitch, against the sensor member 24. The angular motion of the sensor member 24 is transferred to the shaft 2, resulting in pulses being generated by the rotary encoder 4, as best shown in FIG. 3. The pulses generated by the rotary encoder 4 is partitioned or grouped into blocks determined by the MSP's sample time, and finally counted. This is the MAPP# of the material.

The MAPP# will vary in direct relationship to the change in gradation of the material. Though the sensor member 24 is not able to penetrate deep into hard material, a significant amount of variation in the MAPP# was detected when the apparatus was subjected to materials found in a concrete mix. The MAPP# produced by each controlled product, i.e. coarse rock, fine rock, Navy and sand, was grouped and separated with enough consistency, making the present invention useful in identifying the particular material on the conveying means at a given moment.

The MSP will now be explained in detail.

Figure 4A:
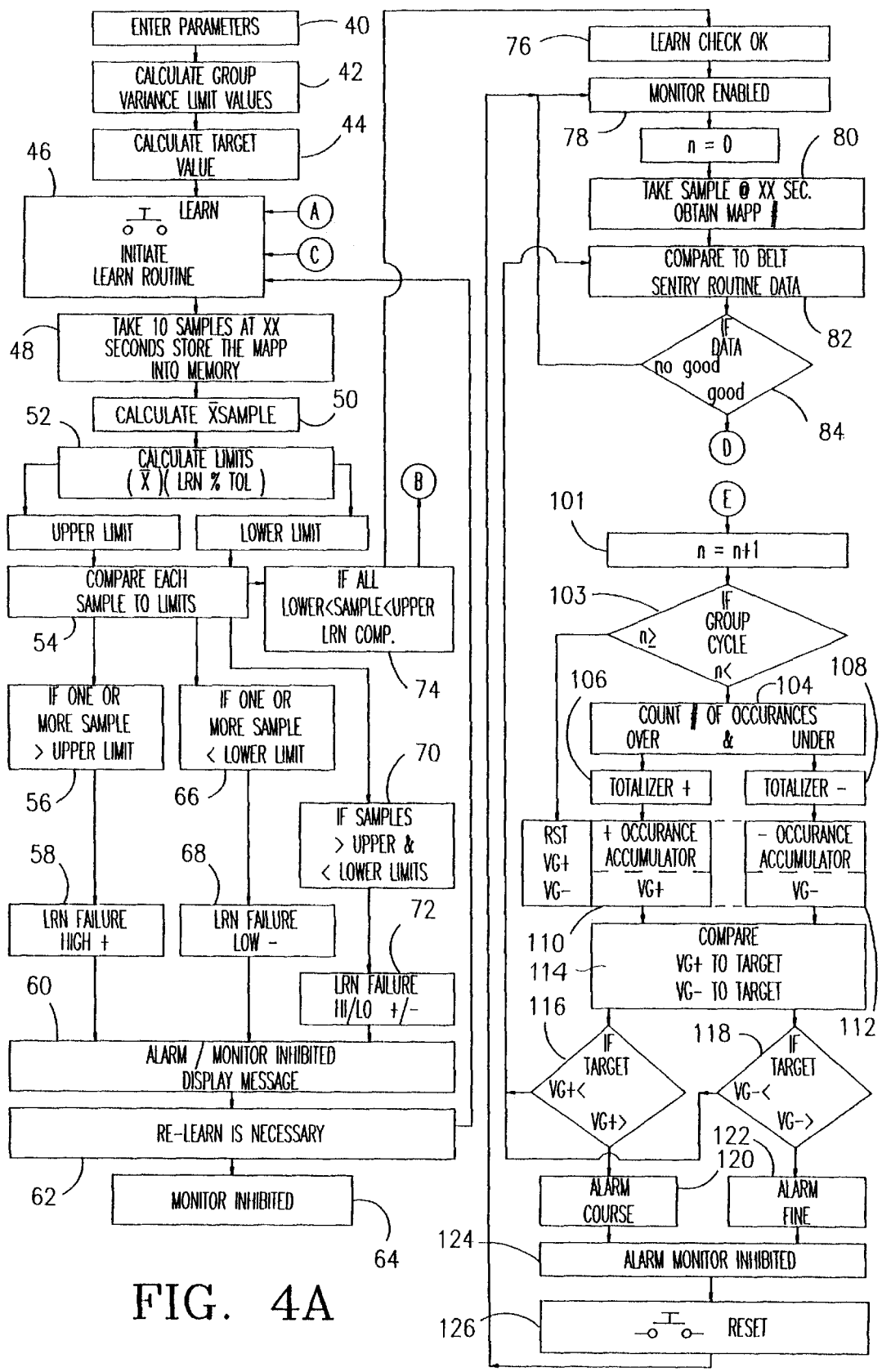

Referring to FIG. 4A, the twelve parameters discussed above are entered at step 40. The group variance limit values are calculated at Step 42. The target value is then calculated at Step 44 from the Failure Percentage.

MODE 1: NORMAL OPERATION LEARN MODE

The LEARN button 34 is depressed momentarily to enable the LEARN routine within the MSP at Step 46.

A representative sample of the controlled product is allowed to work the sensor member 24 for the length of time greater than 10, the number of samples to LEARN (a constant set by the MSP), multiplied by the LEARN TIME parameter entered previously via the operator interfaced terminal 30 in XX seconds. The length of the sample on the conveying means must be greater in time than 10 times the LEARN TIME, or Sample Length (in seconds)>10×Learn Time, for the MSP to complete a successful LEARN routine. If the sample length or the available length of material to be LEARNED on the conveying means is less than the total time it takes for the MSP to sample it, the LEARN reference will not be a true representative of the material. Therefore, Sample Length (in seconds)>10×Learn Time.

Each sample for XX seconds (Learn Time) produces a MAPP# which is stored into memory. Thus, there will be ten MAPP#'s. Each one is a result of the sensor member 24 working off the material. This will be identified as MAPP#L, MAPP#2, MAPP#3, . . . MAP#10. The samples are taken at Step 48.

LEARN CHECK

Following the taking of the ten samples, the MSP proceeds to check each LEARNED MAPP#, i.e. MAPP#1, MAPP#2 . . . MAPP#10, against any extreme variations outside the limits set by the LEARN % TOLERANCE parameter. The MSP first arrives at the limits by computing the average MAPP# generated by the ten samples, multiplied by the LEARN % TOLERANCE, and finally adding and subtracting the result to produce the upper and lower limits, at steps 50 and 52. The average is calculated as follows.

(MAPP#1+MAPP#2+ . . . +MAPP#10)/10=MAPP# Average MAPP# Average×LEARN % TOLERANCE= LEARN TOLERANCE MAPP# Ave.−LEARN TOL.<Check<LEARN TOL.+MAPP# Ave.

Each MAPP#, i.e. MAPP#1, MAPP#2... MAPP#10, is now compared or checked against both limits by the MSP and is accepted if within the margins, or an alarm is set off if found to be outside the range. The limits are calculated at Step 52 and each sample is compared to the limits at Step 54. If one or more of the samples exceeds the upper limit at Step 56, the MSP will output a message at the operator interface terminal 30, "LEARN FAIL:+" at Step 58, and the MSP will cause an alarm at Step 60 and a message, "Re-LEARN is necessary" will be displayed at the operator interface terminal 30, at Step 62. The MONITORING mode is then inhibited at Step 64.

If one or more of the samples fall below the lower limit at Step 66, then the operator interface terminal will output a display, "LEARN FAIL:−" at Step 68 an alarm will be initiated at Step 60 and display a message, "Re-LEARN is Necessary" at Step 62. The MONITORING mode is inhibited at Step 64.

If the samples fall above and below the upper limits at Step 70, the operator interface terminal 30 will display a message, "LEARN FAIL:+−" at Step 72 and the MSP will cause an alarm and display the message, "Re-LEARN is necessary" in the operator interface terminal 30, at Step 62. The MONITORING mode of the MSP is inhibited at Step 64. The LEARN routine advantageously provides a means for determining whether the apparatus will work for the specific product.

If all the samples fall within the range of the lower and upper limits at Step 74, the operator interface terminal 30 will display a message, "LEARN CHECK OK" at Step 76 and the MSP will then enter the MONITORING mode at Step 78. The MSP will now recognize and process the MAPP#'s to be generated during the MONITORING mode.

CONVEYOR (BELT) SENTRY ROUTINE

Following the LEARN CHECK routine and MONITORING is enabled, the MSP will enter the BELT SENTRY routine. The routine will compare the present MAPP# against a minimum MAPP# necessary to indicate that there is in fact material on the belt and that the material is not dribbling or sporadically being thrown onto the belt or being caused by any other random occurrences. This is done by causing the MSP compare the MAPP# against the lower LEARN CHECK MARGIN or,

MAPP# AVERAGE–LEARN TOLERANCE.

The MSP will take a sample at XX sec. and obtain a MAPP# at Step 80 and compare the sample to the BELT SENTRY routine data at Step 82. The MSP will only allow the MAPP# for further processing only if it detects a MAPP# greater than the value (lower LEARN CHECK margin) continuously for a period of time in seconds at Step 84. In other words, the MSP will recognize the presence of valid material working the sensor member 24 and not random hits by stray objects, trailing debris, conveying means connections, etc, only if it detects a MAPP# greater than the value continuously for a period of time in seconds.

Figure 4B:
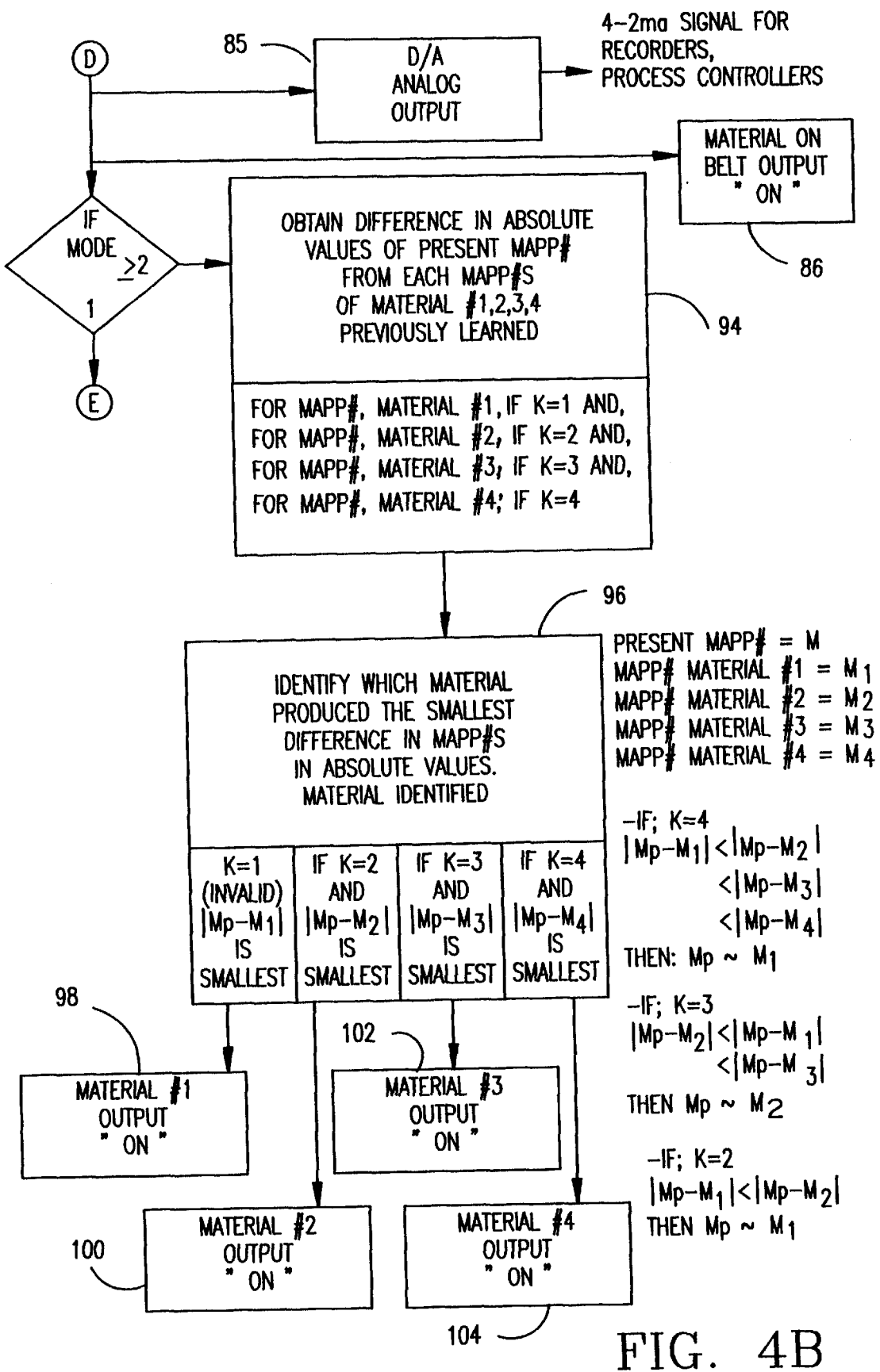

If the present MAPP# fails the BELT SENTRY routine, the MSP will display a message, "MAPP FAIL STAND BY", via the operator interface terminal 30 and the processing circuits are disabled and the system put into STAND BY. If the present MAPP# passes the BELT SENTRY routine, the MSP will display a message, "MONITORING" via the operator interface terminal 30. The processing circuits are then enabled and the present MAPP# is further processed to provide additional information. Analog output, such as 4–20 ma signal, is provided at step 85 to drive recorders, process controllers, etc., as best shown in FIG. 4B. The presence of valid material on the conveying means is indicated at Step 86, as best shown in FIG. 4B.

MONITORING

A sample is taken from the material on the conveying means for a time period set by the LEARNING/SAMPLE TIME of the MSP previously entered at Step 40 and generates a MAPP#. The MAPP# generated by the MSP from the sample is then compared to each of the ten samples taken during the LEARN cycle, whether the number is above (VG+) or below (VG–) the ten LEARNED sample data. The counter is incremented at step 101 until n samples for the group cycle have been taken at step 103.

The number of occurrences resulting from the comparison, greater or less than the present MAPP#, is counted at Step 104 and stored in variation group registers VG+ and VG– respectively, at Steps 106, 108, 110 and 112. Both VG+ and VG– registers are accumulated and displayed on the operator interface terminal 30. The numbers stored in the VG+ and VG– registers are compared to the respective target at Step 114. If the VG+ and VG– registers are below the targets at Steps 116 and 118, the monitoring cycle is repeated at Step 80 for the number of times designated by the GROUP CYCLE parameter previously entered at Step 40.

Both VG+ and VG– registers accumulate the number of greater and less than occurrences from the comparison routine within a group cycle. The maximum number of occurrences, either greater than or less than is equal to, 10 samples×group cycle If 6 cycles (meaning 6 samples are taken for each group) are designated as a group, then the maximum number of occurrences beyond either limit would be 60.

The MSP next calculates the TARGET which is also displayed on the operator interface terminal 30. The TAR-GET is the maximum allowable occurrences per group. This is obtained by multiplying the FAILURE % parameter by the maximum number of occurrences. For example,

10 SAMPLES×GROUP CYCLE×FAILURE %=TARGET.

An alarm occurs either at Step 120 or 122 anytime either VG+ or VG– exceeds the TARGET before the registers are reset to start a new group. A message on the operator interface terminal 30 will also be displayed, describing the direction of the gradation drift anytime either VG+ or VG– exceeds the TARGET prior to a reset, which is to start another accumulation of VG+ and VG– within a GROUP CYCLE. If VG– exceeds the TARGET, the OIT will display the message, "COARSE" indicating that the material has become coarser. If VG– exceeds the TARGET the operator interface terminal 30 will display the message, "FINE" indicating that the material has become finer. The MSP will also alarm at Step 124, indicating that the monitoring has been inhibited and that the reset button at Step 126 will have to be enabled to start the monitoring mode.

The MSP will reset both VG+ and VG– to 0 if the result of the last sample belonging to the group (the CYCLE GROUP parameter value) did not cause either register to exceed the TARGET.

The MSP also provides 2 totalizers which continue to accumulate VG+ and VG– registers, which can be used to observe the balance or the drift of the material over a period of time. These two totalizers are also displayed on the operator interface terminal 30 and resetable via the reset button 34 on the control panel 32.

An analog output is provided for recording and process control purposes.

It will be seen from the above that the output of the rotary encoder 4 in pulses is used to generate a number based on the angular swinging motion of the sensor member 24 as it interacts with the moving product on the conveying means below. This number is then used to detect and record increasing gradation changes the product, such as crushable rock, which can then in turn be used as a feedback device to warn of crusher close side setting opening or for automatically adjusting crusher openings. With this number, the apparatus of the present invention can also detect material contamination in a quarry operation feed mill, or processing plant, before someone or something realizes the mess. It can also be used to detect the presence of different feed products in a feed mill operation, such as sugar and flower etc.

MODE 2: MULTIPLE MATERIAL IDENTIFICATION

The multiple material identification mode is used whenever the user elects to identify a material from among several materials that have been LEARNED before using the LEARN routine. The present invention illustrates LEARNING four materials, but any number is applicable, depending on the user's situation.

Figure 4C:
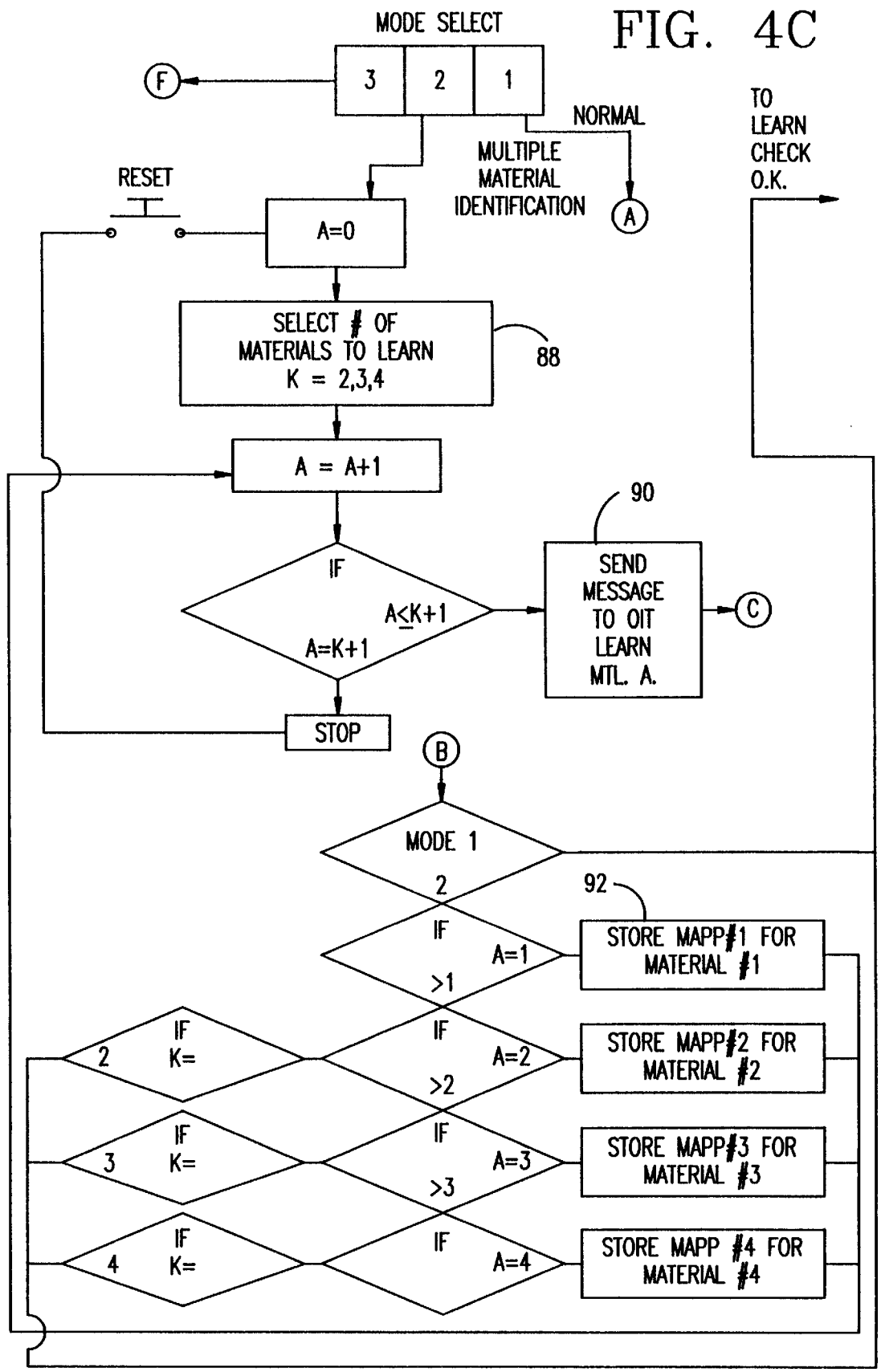

Referring to FIG. 4C, the MSP scans the # MTL LRN parameter at step 88. The MSP send a message to the OIT 30 at step 90 to begin LEARN routine for Material #1. The user must have on the conveyor at this time one of the materials that is to be identified. The first material will be labeled as Material #1 by the MSP. When ready the user initiates the LEARN routine at step 46 by depressing the LEARN button 34. The MSP enters the LEARN routine and stores the resulting MAPP# as Material #1 MAPP# at step 92.

The process repeats itself for the second, third and fourth materials with similar messages and prompts, with the user depressing the learn button 34 when ready with the respective material moving on the conveyor until the # MTL LRN parameter is satisfied, as best shown in FIG. 4C.

Upon satisfying the # MTL LRN parameter, the MSP will go into the MONITORING mode, as in Mode #1, bypass the VG decision making steps and go directly into finding the difference between the present MAPP# and the LEARNED MAPP#'s for the several materials now stored in memory as Material #1 MAPP#, Material #2 MAPP#, Material #3 MAPP#, and Material #4 MAPP#, or less, depending on the # MTL LRN parameter, as best shown in step 94 of FIG. 4B.

The difference between the present MAPP# and the Material MAPP# is in absolute values, i.e., the smaller MAPP# will always be subtracted from the larger MAPP# to produce positive result or difference. Once all the differences are obtained from each Material MAPP#, the MSP will identify the present material on the conveyor by the Material MAPP# that resulted in the smallest difference, shown at step 96. The MSP outputs a signal at steps 98, 100, 102 and 104 on the respective Material #1, #2, #3, or #4 output, identifying which material is presently on the conveyor.

MODE 3: COMPARATOR

Figure 4D:
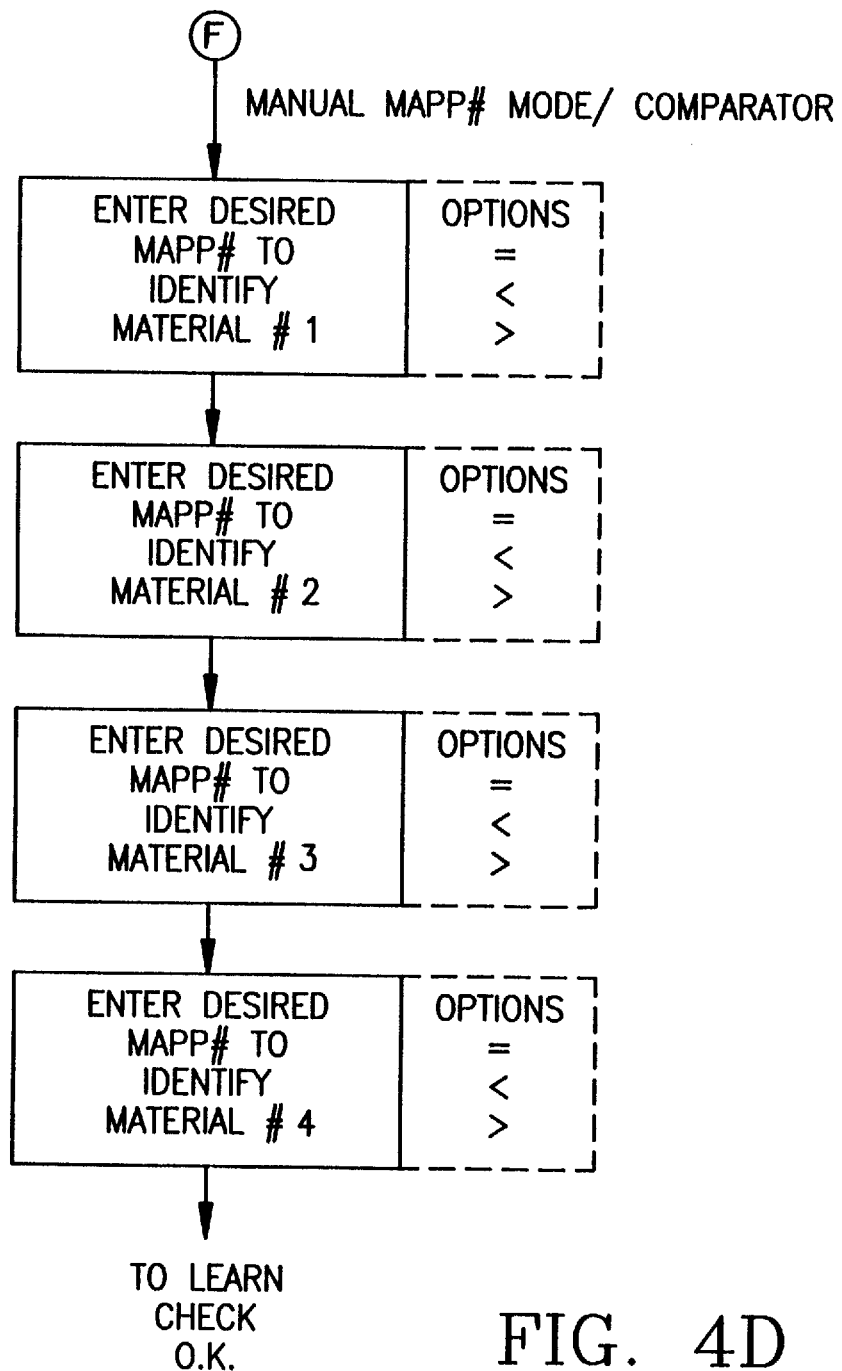

As in Mode 2, the VG decision making steps are bypassed in Mode 3. Referring to FIG. 4D, Mode 3 utilizes the Material #1, #2, #3, and #4 MAPP#'s along with an option comparator signs =, <, > to design comparative regions between Material # MAPP#'s, or windows, or equalities for specialized alarm applications. For example, Material #1 MAPP# <. If the present MAPP# is greater than the material #1 MAPP#, Material #1 output will be ON.

Material #2 MAPP# =. If the present MAPP# is equal to Material #2 MAPP#, Material #2 output will be ON.

Material #3 MAPP# >. If the present MAPP# is less than Material #3 MAPP#, Material #3 output will be ON.

With several outputs wired in series or parallel, the desired comparison, region or window is achieved.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. An apparatus for detecting marginal gradation changes of a controlled product on a conveyor, comprising:
   a) a transducer for converting swinging motion to a number of pulses;
   b) a member operably secured to said transducer, said member for being in contact with the controlled product to cause said member to swing back and forth, thereby causing said transducer to generate the number of pulses; and
   c) a programmable device operably connected to said transducer, said device being adapted to count the number of pulses generated by said transducer over several blocks of time periods, compare the number in each block of time to a predetermined group of reference numbers for the product, sum the number of occurrences that the number is above or below the group of reference numbers and provide an output when the sum exceeds a predetermined target value.

2. An apparatus as in claim 1, wherein:
   a) said transducer is a rotary encoder sensor.

3. An apparatus as in claim 2, and further comprising:
   a) a shaft operably connected to said rotary encoder sensor; and
   b) said member is secured to said shaft.

4. An apparatus as in claim 3, wherein:
   a) said member is removable from said shaft.

5. An apparatus as in claim 3, wherein:
   a) said member is secured transversely to said shaft.

6. An apparatus as in claim 1, wherein:
   a) said member is selectively vertically positionable above the product.

7. An apparatus as in claim 1, wherein:
   a) said programmable device includes a programmable logic controller.

8. An apparatus as in claim 1, wherein:
   a) said programmable device includes a program for generating said group of reference numbers for the product; and
   b) said program includes the steps of taking a number of samples, counting the number of pulses in each sample, comparing the number of pulses in each sample to a predetermined tolerance, and accepting the samples only if they all fall within the predetermined tolerance, whereby the number of pulses in the accepted group of samples comprises said group of reference numbers.

9. An apparatus as in claim 3, and further comprising:
   a) a frame adapted to secure said transducer and said member above the product.

10. An apparatus as in claim 9, wherein:
    a) said frame includes a pair of vertical channel members for being secured to the conveyor; and
    b) a mounting plate secured between said pair of vertical channel members.

11. An apparatus as in claim 10, wherein:
    a) said shaft is secured to said mounting plate.

12. An apparatus as in claim 10, wherein:
    a) said rotary encoder sensor is secured to said mounting plate.

13. An apparatus for identifying a product on a conveyor, comprising:
    a) a transducer for converting swinging motion to a number of pulses;
    b) a member operably secured to said transducer, said member for being in contact with the controlled product to cause said member to swing back and forth, thereby causing said transducer to generate the number of pulses; and
    c) a programmable device operably connected to said transducer, said device being adapted to count the number of pulses over a period of time generated by said rotary encoder sensor, compare the number to a predetermined reference number for the product, and indicate that the product is present on the conveyor when the number of pulses is greater than the reference number.

14. An apparatus as in claim 13, wherein:
    a) said transducer is a rotary encoder sensor.

15. An apparatus as in claim 13, and further comprising:
    a) a shaft operably connected to said transducer; and
    b) said member is secured to said shaft.

16. An apparatus as in claim 13, wherein:
   a) said programmable device includes a programmable logic controller.

17. An apparatus as in claim 13, wherein:
   a) said programmable device includes a program for generating the reference number for the product; and
   b) said program includes the steps of taking a number of samples, counting the number of pulses in each sample, averaging the samples, calculating a lower limit based on a preselected tolerance, whereby the lower limit number comprises said reference number.

18. A method for detecting marginal gradation changes in a controlled product on a conveyor, comprising the steps of:
   a) contacting the moving product with a sensor member;
   b) allowing the sensor member to swing back and forth as it contacts the moving product;
   c) converting the swinging motion of the sensor member to a number;
   d) comparing the number to a group of predetermined reference numbers for the product;
   e) repeating steps c) and d) over several blocks of time;
   f) summing the number of occurrences that each number is above or below the group of reference numbers; and
   g) providing an indication when the sum exceeds a predetermined target value.

19. A method as in claim 18, wherein:
   a) said converting step is implemented with a rotary encoder sensor.

20. A method for detecting the presence of a product on a conveyor, comprising the steps of:
   a) contacting the moving product with a sensor member;
   b) allowing the sensor member to swing back and forth as it contacts the moving product;
   c) converting the swinging motion of the sensor member to a number;
   d) comparing the number to a predetermined reference number; and
   e) providing a physical indication when the number is greater than the reference number.

21. An apparatus for identifying a product on a conveyor, comprising:
   a) a transducer for converting swinging motion to a number of pulses;
   b) a member operably secured to said transducer, said member for being in contact with the controlled product to cause said member to swing back and forth, thereby causing said transducer to generate the number of pulses; and
   c) a programmable device operably connected to said transducer, said device being adapted to count the number of pulses over a period of time generated by said rotary encoder sensor, compare the number to a predetermined group of numbers, each of which corresponds to a product expected to be on the conveyor, and indicate the particular product whose number is closest to the number of pulses.

22. An apparatus for comparing a product on a conveyor to a reference product, comprising:
   a) a transducer for converting swinging motion to a number of pulses;
   b) a member operably secured to said transducer, said member for being in contact with the controlled product to cause said member to swing back and forth, thereby causing said transducer to generate the number of pulses; and
   c) a programmable device operably connected to said transducer, said device being adapted to count the number of pulses over a period of time generated by said rotary encoder sensor, compare the number of pulses to a predetermined number indicative of the reference product, and indicate whether the product is the same as, greater or less than the reference product.

\* \* \* \* \*